United States Patent
Curtis

(10) Patent No.: US 8,951,204 B2
(45) Date of Patent: Feb. 10, 2015

(54) METHOD FOR USING A PULSE OXIMETRY SIGNAL TO MONITOR BLOOD PRESSURE

(75) Inventor: Guy P. Curtis, San Diego, CA (US)

(73) Assignee: The Guy P. Curtis and Frances L. Curtis Trust, San Diego, CA (US)

( * ) Notice: Subject to any disclaimer, the term of this patent is extended or adjusted under 35 U.S.C. 154(b) by 377 days.

(21) Appl. No.: 13/464,732

(22) Filed: May 4, 2012

(65) Prior Publication Data

US 2013/0296671 A1 Nov. 7, 2013

(51) Int. Cl.
*A61B 5/02* (2006.01)
*A61B 5/021* (2006.01)
*A61B 5/022* (2006.01)

(52) U.S. Cl.
CPC ......... *A61B 5/02116* (2013.01); *A61B 5/02225* (2013.01); *A61B 2560/0223* (2013.01)
USPC ...................................................... 600/485

(58) Field of Classification Search
CPC ... A61B 5/021; A61B 5/0205; A61B 5/14551
USPC .................................................. 600/324, 485
See application file for complete search history.

(56) References Cited

U.S. PATENT DOCUMENTS

| | | | |
|---|---|---|---|
| 5,776,071 A * | 7/1998 | Inukai et al. ................... | 600/493 |
| 5,865,756 A * | 2/1999 | Peel, III .......................... | 600/490 |
| 5,971,932 A | 10/1999 | Okamoto | |
| 6,527,725 B1 * | 3/2003 | Inukai et al. ................... | 600/485 |
| 6,547,742 B2 * | 4/2003 | Oka et al. ....................... | 600/485 |
| 6,801,798 B2 * | 10/2004 | Geddes et al. ................ | 600/323 |
| 7,300,404 B1 | 11/2007 | Kolluri et al. | |
| 2002/0038090 A1 * | 3/2002 | Sunagawa et al. ............ | 600/485 |
| 2004/0077934 A1 * | 4/2004 | Massad ......................... | 600/300 |
| 2009/0018453 A1 * | 1/2009 | Banet et al. ................... | 600/493 |
| 2010/0087744 A1 | 4/2010 | Licata | |

OTHER PUBLICATIONS

Gavish. Repeated Blood Pressure Meaurements May Probe Directly an ARterial Property. Arterial Structure and Compliance, Apr. 2000, vol. 13, No. 4, Part 2.*
PCT International Search Report, Application No. PCT/US2013/038363, Apr. 26, 2013.

* cited by examiner

*Primary Examiner* — Etsub Berhanu
(74) *Attorney, Agent, or Firm* — Nydegger & Associates

(57) ABSTRACT

A system for continuously monitoring the blood pressure of a patient over an extended time interval requires using a blood pressure measuring unit (e.g. a sphygmomanometer) to calibrate an oximeter. Specifically, the oximeter is used to continuously detect and measure amplitudes for each blood flow pulse of the patient. Periodically, the sphygmomanometer is used to measure blood pressures (systolic and diastolic) in an artery of the patient. Immediately after the measurement cycle is completed, a computer correlates the measured systolic pressure with the pulse amplitude that is detected by the oximeter. Thereafter, the pulse amplitudes that are detected by the oximeter are used as indications of variations in the systolic pressure during the extended time interval that follows.

15 Claims, 1 Drawing Sheet

METHOD FOR USING A PULSE OXIMETRY SIGNAL TO MONITOR BLOOD PRESSURE

FIELD OF THE INVENTION

The present invention pertains generally to devices for monitoring the blood pressure of a patient. More particularly, the present invention pertains to devices that continuously, or intermittently, monitor the blood pressure of a patient over an extended period of time. The present invention is particularly, but not exclusively, useful as a system and method for periodically calibrating an oximeter to provide uninterrupted indications of blood pressure, where the oximeter pulse is a faithful surrogate for blood pressure determined by routine measures (sphygmomanometer cuff or interarterial catheter).

BACKGROUND OF THE INVENTION

There are many situations in a medical facility when an ability to continuously monitor a patient's blood pressure is very important. For instance, during surgical procedures in an operating room an ability to continuously monitor blood pressure may be of utmost importance. In such situations an ability to detect a trending change in the blood pressure of a patient may be helpful to avert adverse outcomes. Moreover, a requirement to intermittently interrupt other activities in order to directly obtain a blood pressure reading by methods now routinely employed may be difficult or cumbersome to accomplish.

Blood pressure readings are typically made with a sphygmomanometer by positioning a pressure cuff around a patient's extremity containing a large artery. For humans, the cuff is usually placed on an arm. Once the cuff has been properly placed, pressure is imposed on the arm by the cuff to occlude the artery. This cuff pressure is then gradually reduced and transduced to first read a pressure at which a turbulent flow of blood begins, and to then read a pressure at the point where turbulence disappears. Systolic pressure is the point where turbulent flow starts and diastolic pressure is the point where turbulent flow ends. Taken together, the systolic and diastolic pressures provide what is commonly referred to as a patient's blood pressure reading. When a stethoscope is used to measure a patient's blood pressure, the Korotkoff sounds are auscultated to identify the systolic and diastolic pressures. From a monitoring stand point an accurate systolic pressure is most important.

In addition to the pressure readings discussed above, it is also well known that the occurrence of each cardiac cycle and resultant blood flow can be detected by an oximeter. The oximeter functions using a photoelectric signal which varies in strength in accordance with oxygenation values as blood pulses through the area of signal origin. Importantly, the amplitudes of the oxygenation values are unique for each pulse, and these values are related directly to the systolic and diastolic blood pressure of the patient.

With the above in mind, it is an object of the present invention to provide a system for monitoring the blood pressure of a patient by continuously measuring blood oxygenation values, and for correlating pulse oxygenation values in each cardiac cycle with the systolic and diastolic pressures of a patient. Another object of the present invention is to provide a system for monitoring the blood pressure of a patient by continuously measuring blood oxygenation values at a point in time and over an extended period of time. Still another object of the present invention is to provide a system and method for continuously monitoring blood pressure that is easy to use and is comparatively cost effective.

SUMMARY OF THE INVENTION

A system for continuously monitoring the blood pressure of a patient combines the use of a blood pressure reading device (e.g. a sphygmomanometer) with the use of a device for monitoring blood oxygenation values (e.g. an oximeter). In this combination, the sphygmomanometer is used to calibrate the signal from the oximeter (pulse wave form) which can then be used to continuously or discontinuously measure the blood pressure. As envisioned for the present invention, these indications are monitored over a predetermined time interval before another calibration of the signal is required. Typically, calibration is accomplished using a sphygmomanometer (or in rare instances, with an interarterial pulse measurement).

By way of background, it is to be appreciated that the oximeter pulse bears an inverse relationship to the sphygmomanometer measurement of blood pressure. In this relationship, the systolic cuff blood pressure is the point at which a small amount of turbulent flow begins to occur; this should produce no detectable flow at the oximeter and will thus represent zero pressure for the oximeter pulse. As cuff pressure is progressively reduced, however, and as blood flow past the cuff increases, there will come a point where a pulse is first detected via the oximeter. This detection represents the diastolic pressure for the pulse oximeter and has a value that is equal to the pressure in millimeters of mercury between this point and the diastolic pressure previously determined by the sphygmomanometer. The diastolic pressure that is determined by the sphygmomanometer should be accompanied by a fully developed oximeter pulse amplitude and should be calibrated with systolic pressure determined by the sphygmomanometer.

Structurally, the system of the present invention includes a unit for periodically measuring the systolic and the diastolic blood pressures in an artery of the patient during a measurement cycle. Specifically, a systolic pressure is measured at the beginning of the measurement cycle and a diastolic pressure is measured at the end of the measurement cycle. This is done by any of several ways, all well known in the pertinent art (e.g. a sphygmomanometer). Typically, in the event, an inflatable cuff is positioned around an arm of a patient and it is then inflated to establish an initial cuff pressure for occluding an artery of the patient. A control value is then selectively operated to release the cuff pressure to allow blood flow through the artery. It is well known that in such an operation, measurements (i.e. readings) of the systolic pressure and the diastolic pressure can be obtained.

Also included in the system is a device (e.g. an oximeter) for detecting blood oxygen content in the cardiovascular system of a patient. Importantly, each pulse that is measured by the oximeter has a unique amplitude which is indicative of the blood oxygenation value at the time of the pulse. Unlike the unit for measuring blood pressure (e.g. sphygmomanometer), however, the device for detecting blood pressure pulses (e.g. oximeter) can be operated continuously.

A computer is provided in the system of the present invention for correlating the pulse amplitude values that are detected by the photoelectric oximeter unit, with a cuff determination of blood pressure measurements that are obtained by the sphygmomanometer. Thereafter, with the correlation that is established by the computer, variations in pulse amplitudes are subsequently detected and these amplitudes are respectively identified as indications of corresponding variations in systolic and diastolic pressures. Such correlations continue during an extended time interval following the measurement cycle. As envisioned for the present invention, the extended time interval may range anywhere from fifteen minutes to several hours. During this extended time interval, a monitor is incorporated to record the indications of systolic pressure that are obtained by computer correlations with the pulse amplitudes detected by the oximeter and the systolic pressure can be presented on a visual display. Significant changes in blood oxygenation should automatically call for a recalibration of the device.

As implied above, calibration of the system essentially requires fitting the pulse responses that are detected by an oximeter, with the blood pressure readings that are obtained by a sphygmomanometer. Once a calibration has been completed, the oximeter alone can be used as an indicator of blood pressure. Subsequent calibrations can then be made periodically or whenever it is deemed necessary. The conduct of a calibration will perhaps be best appreciated from a temporal perspective.

Initially, both the sphygmomanometer and the oximeter need to be properly positioned on the patient. Specifically, the sphygmomanometer is positioned on an upper arm of the patient, and the oximeter is positioned on a finger of the same arm. The cuff of the sphygmomanometer is then inflated until the artery in the arm is occluded and blood flow into the arm has ceased. With this initial set-up, there is no blood pressure reading (sphygmomanometer) and there is no pulse response (oximeter).

An actual calibration of the system begins at a time "$t_0$", when the cuff pressure has been reduced to the point where blood begins a turbulent flow through the artery of the arm. It is at this time, "$t_0$", that the first Korotkoff sounds are heard to indicate the patient's systolic pressure "$p_{systolic}$". The cuff pressure is then further reduced until, at a time "$t_1$", a first pulse value "$V_1$" is detected by the oximeter. Note: "$V_1$" represents the minimum pressure pulse amplitude that can be determined by the pulse oximeter (i.e. it represents the lower limit of pressure differential that is detectable by the oximeter). Further, at the time "$t_1$", as $V_1$ is detected, the blood pressure reading from the sphygmomanometer "$p_1$" is also taken. Using the value of "$p_1$", an initial drop in blood pressure "$\Delta_1$" from the measured systolic pressure "$p_{systolic}$" at time "$t_0$" to the measured blood pressure "$p_1$" at time "$t_1$" can be determined (i.e. $\Delta_1 = p_{systolic} - p_1$). At this point it is to be noted that "$p_{systolic}$" is related to "$p_1$" by the value of the blood pressure drop "$\Delta_1$". Thus, $\Delta_1$ is a compensating factor that will eventually be used to correct "$V_1$" (i.e. after $V_1$ has been converted to pressure metrics).

As the first pulse value ($V_1$), the blood pressure reading ($p_1$) and the blood pressure drop ($\Delta_1$) are established at time "$t_1$", the cuff pressure is further reduced. This reduction in cuff pressure continues until, at a time "$t_2$", the Korotkoff sounds stop to indicate that blood flow in the arm has returned to normal and is fully developed. It is at the time "$t_2$" that the patient's diastolic pressure "$p_{diastolic}$" is measured (i.e. the Korotkoff sounds stop). Also, a second pulse value "$V_2$" indicating the fully developed oximetry pulse is detected by the oximeter at the time "$t_2$". The difference between the pulse values $V_1$ and $V_2$ is then established as a pulse differential "$\Delta_v$".

Importantly, the pulse differential "$\Delta_v$" ($\Delta_v = V_2 - V_1$) corresponds directly to the pressure differential "$\Delta_p$" that is measured by the sphygmomanometer as a drop from the pressure "$p_1$" at time "$t_1$" to the "$p_{diastolic}$" measured at time "$t_2$" (i.e. $V_2 - V_1 \sim p_1 - p_{diastolic}$). Stated differently, $\Delta_p$ corresponds directly to $\Delta_v$. Thus, $\Delta_p$ can be compared to $\Delta_v$ to correlate the pulse metrics of $\Delta_v$ to the pressure metrics of $\Delta_p$. Based on this correspondence, the units of pulse value (oxygenation level) that are measured by the oximeter can be directly converted to units of pressure (mm Hg) that are measured by the sphygmomanometer.

With oximeter detections (i.e. pulse values "V") that have been converted to the same scale as blood pressure measurements (i.e. mm Hg), the following relationships are of particular importance. First, the pulse value "$V_1$", which is measured by the oximeter at time "$t_1$", corresponds directly to the patient's diastolic pressure "$p_{diastolic}$". Also, the patient's systolic pressure "$p_{systolic}$" corresponds to the pulse value "$V_2$", which is measured by the oximeter at time "$t_2$", plus the correction factor $\Delta_1$ (i.e. $p_{systolic} = V_2 \Delta_1$). The consequence of this is that only the oximeter is needed to monitor blood pressure (i.e. $p_{systolic} = V_2 + \Delta_1$, and $p_{diastolic} = V_1$). As noted above, after a calibration, the sphygmomanometer needs to be used only when there is a demonstrated or scheduled need for another calibration.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
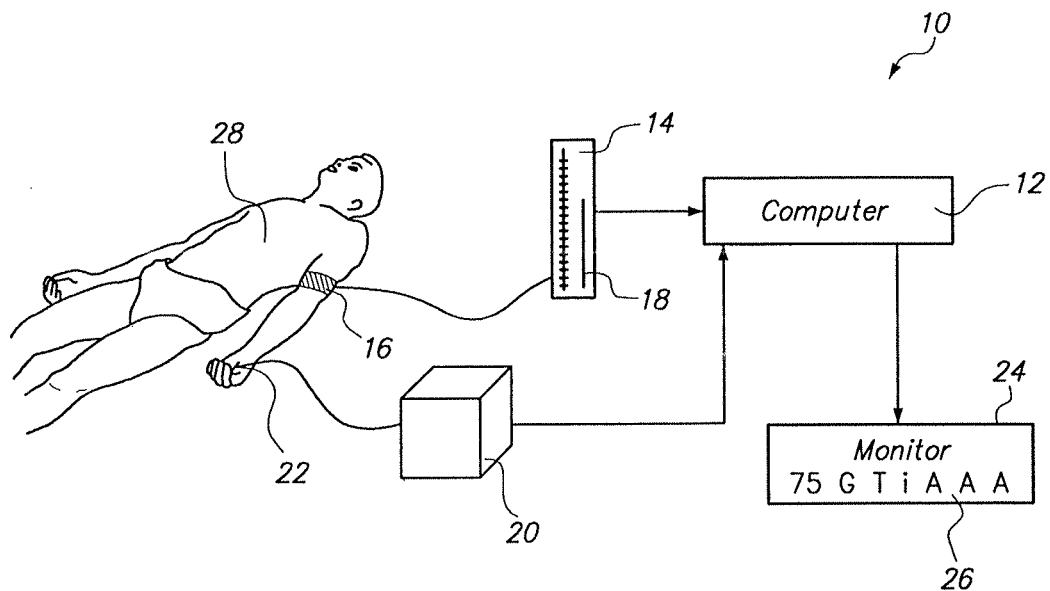
FIG. 1 is a schematic presentation of the components used in an operation of the present invention.

Referring initially to FIG. 1, a system for continuously monitoring the blood pressure of a patient is shown and is generally designated 10. As shown, the system 10 includes a computer 12 that is connected with a pressure unit 14. Included in the pressure unit 14 is an inflatable cuff 16 that is connected directly to a manometer 18. Alternatively, rather than a manometer 18, it will be appreciated by the skilled artisan that the present invention may incorporate an aneroid device for the same purpose. In either case, as envisioned for the present invention, the pressure unit 14 is functionally the same as, or is similar to, a common sphygmomanometer or interarterial catheter.

Also included in the system 10 is a pulse detector 20. Preferably, the pulse detector 20 is an oximeter of a type well known in the pertinent art for taking oxygenation readings (hereinafter, the pulse detector 20 may sometimes be referred to as oximeter 20). As shown in FIG. 1 a sensor 22 is incorporated as part of the oximeter 20, and the oximeter 20 is connected directly to the computer 12. Further, the computer 12 is connected to a monitor 24 that may include a visual display 26.

In preparation for an operation of the present invention, the inflatable cuff 16 is properly positioned on a patient 28. In FIG. 1, this positioning is shown to be on the left arm of the patient 28. Additionally, the sensor 22 is positioned on a finger of the patient 28. With these connections, the system 10 is ready for calibration and/or operation.

Figure 2:
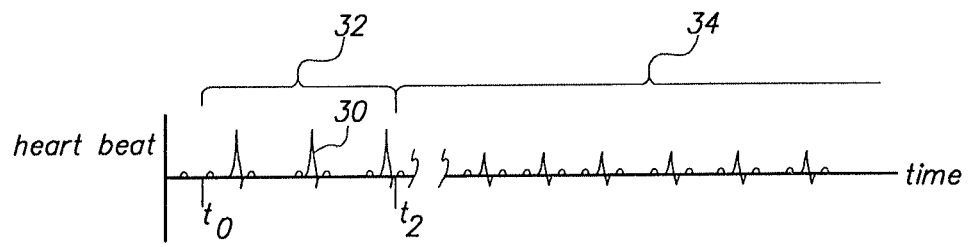
FIG. 2 is a representative time line graph for the heartbeat of a patient.
Figure 3:
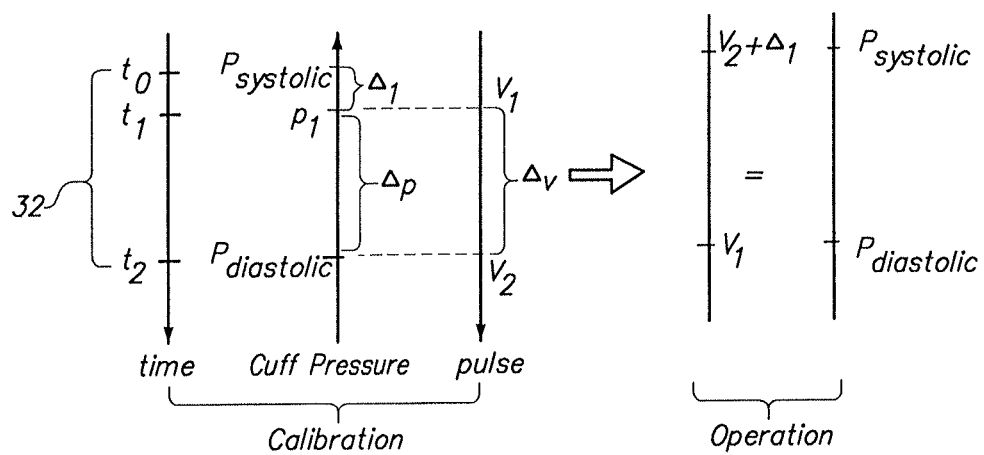
FIG. 3 is a graphical representation of pressure and pulse measurements required for calibration and operation of the present invention.

In review, FIG. 2 shows a typical graph for heart beats 30 of a patient 28. For purposes of disclosure, the heart beats 30 are shown to extend through a measurement cycle 32 and, after the measurement cycle 32, on into an extended period of time 34. Both FIG. 2 and FIG. 3 show that the measurement cycle 32 begins at a time $t_0$ and ends at a time $t_2$. As envisioned for the present invention, the extended period of time 34 will start at the time $t_2$ and may continue for as long as a few hours. Further, it is envisioned that the extended period of time 34 may actually include several intermittent continuous intervals of time. In any event, during the extended period of time 34 the pulse of each heart beat 30 will provide pulse values "V", that are detected by the pulse detector (oximeter) 20. These pulse values "V" are then correlated with blood pressure readings for a systolic pressure "$p_{systolic}$" and a diastolic pressure "$p_{diastolic}$" that were taken during the measurement cycle 32. With this in mind, the pulse detector (oximeter) 20 needs to be calibrated. A calibration of the system 10 for such an operation is best appreciated with reference to FIG. 3.

In FIG. 3, the description of a calibration for the system 10 is best appreciated in a temporal context. To begin, the patient 28 is connected with the system 10 substantially as shown in FIG. 1. More specifically, the inflatable cuff 16 and the sensor 22 are positioned on the patient 28 in an arrangement of system 10 that is only exemplary. As indicated, with this arrangement, the measurement cycle 32 begins at time $t_0$.

With reference to FIG. 3, a calibration begins at the time $t_0$ when the pressure unit 14 measures the systolic pressure ($p_{systolic}$) of the patient 28. After $t_0$, the cuff pressure that is being detected by the inflatable cuff 16 is reduced from $p_{systolic}$ to a pressure $p_1$. More specifically, the pressure $p_1$ is measured when the pulse detector (oximeter) 20 first senses a pulse value $V_1$. This occurs at the time $t_1$. Note: no pulse values are detected by the pulse detector (oximeter) 20 during the time interval from $t_0$ to $t_1$. With this in mind, two essential measurements are made at the time $t_1$. One is the pulse value $V_1$ which is the lowest pulse value detected by the oximeter 20. The other is an initial pressure drop ($\Delta_1$) which is the difference between $p_{systolic}$ and $p_1$ ($\Delta_1=p_{systolic}-p_1$).

Still referring to FIG. 3, the next significant event in the measurement cycle 32 occurs at the time $t_2$ when the pressure unit 14 measures the diastolic pressure ($p_{diastolic}$) of the patient 28. At time $t_2$, in addition to obtaining a measurement from the pressure unit 14 for $p_{diastolic}$, the pulse detector (oximeter) 20 obtains a pulse value $V_2$. In particular, the pulse value $V_2$ is the highest pulse value detected by the oximeter 20, and it will occur when the heart cycle has again become fully developed.

Using the operational parameters obtained during the measurement cycle 32 at times $t_0$, $t_1$ and $t_2$ as inputs, the computer 12 establishes an operational configuration for the system 10. In detail, a pulse differential "$\Delta_v$" ($\Delta_v=V_1-V_2$) and a pressure differential "$\Delta_p$" ($\Delta_p=p_1-p_{diastolic}$) are calculated by the computer 12. Because the pulse and pressure differentials (i.e. $\Delta_v$ and $\Delta_p$) are directly proportional to each other, their relationship can be used by the computer 12 to correlate the pulse metrics of $\Delta_v$ with the pressure metrics of $\Delta_p$. Stated differently, pulse values "V" obtained from the pulse detector (oximeter) 20 can be used as equivalents of pressure readings taken from the pressure unit 14. Accordingly, as indicated in FIG. 3 for an operation of the system 10, $p_{systolic}$ is equated with $V_2+\Delta_1$ and $p_{diastolic}$ is equated with $V_1$. Thus, during the extended time period 34, the pulse detector (oximeter) 20 can be used alone to provide blood pressure readings for the visual display 26 on monitor 24.

While the particular Method for Using a Pulse Oximetry Signal to Monitor Blood Pressure as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for continuously monitoring the blood pressure of a patient for an extended period of time which comprises:
   a unit for measuring blood pressures in an artery of the patient during a measurement cycle, wherein the measurement cycle has a beginning and an end, and wherein a systolic pressure ($p_{systolic}$) is measured at a time "$t_0$" at the beginning of the measurement cycle and a diastolic pressure ($p_{diastolic}$) is measured at the end of the measurement cycle;
   a device for detecting blood pressure pulses in the cardio-vasculature of a patient during the measurement cycle, wherein a first pulse near the beginning of the measurement cycle has an amplitude value "$V_1$", and a second pulse with an amplitude value "$V_2$" is detected at the end of the measurement cycle wherein $V_1$ is detected by the detecting device and a first pressure $p_1$ is measured by the measuring unit at a determined time ("$t_1$") in the measurement cycle, and wherein an initial pressure drop $\Delta_1$ is established at the time $t_1$, with $\Delta_1$ being a correction factor equal to the difference between $p_{systolic}$ and $p_1$ ($\Delta_1=p_{systolic}-p_1$); and
   a computer for correlating the systolic pressure ($p_{systolic}$) with "$V_2+\Delta_1$", to establish a correlation therebetween, and for thereafter using the correlation to identify variations in pulse amplitudes $V_2$ detected by the detecting device as indications of corresponding variations in systolic pressures ($p_{systolic}$) during the extended period of time following the measurement cycle.

2. A system as recited in claim 1 wherein the computer compares a pulse differential "$\Delta_v$" ($\Delta_v=V_1-V_2$) directly with a pressure differential "$\Delta_p$" ($\Delta_p=p_1-p_{diastolic}$) to correlate pulse metrics of $\Delta_v$ with pressure metrics of $\Delta_p$.

3. A system as recited in claim 2 wherein $p_{systolic}$ is equated with $V_2+\Delta_1$ and $p_{diastolic}$ is equated with $V_1$.

4. A system as recited in claim 3 further comprising a monitor for presenting the indications of systolic pressure during the extended period of time.

5. A system as recited in claim 3 wherein the detecting device is an oximeter and the measuring unit is a sphygmomanometer.

6. A system as recited in claim 3 wherein the extended period of time is greater than fifteen minutes.

7. A system as recited in claim 3 wherein the pulse amplitude values $V_1$ and $V_2$ are detected continuously during the extended period of time.

8. A method for continuously monitoring the blood pressure of a patient for an extended period of time which comprises the steps of:
   measuring blood pressures in an artery of the patient with a unit during a measurement cycle, wherein a systolic pressure ($p_{systolic}$) is measured at a time "$t_0$" at the beginning of the measurement cycle and a diastolic pressure ($p_{diastolic}$) is measured at a time "$t_2$" at the end of the measurement cycle;
   detecting blood pressure pulses in the cardio-vasculature of the patient with a device, wherein each pulse has a pulse amplitude;
   detecting a pulse amplitude value "$V_1$" at a determined time "$t_1$";
   establishing an initial pressure drop "$\Delta_1$", from $p_{systolic}$ to $p_1$, at the determined time "$t_1$" using a computer;
   detecting a pulse amplitude value "$V_2$" at the time "$t_2$"; and using the computer to compare a pulse differential "$\Delta_v$" ($\Delta_v = V_1 - V_2$) directly with a pressure differential "$\Delta_p$" ($\Delta_p = p_1 - p_{diastolic}$) to correlate pulse metrics of $\Delta_v$ with pressure metrics of $\Delta_p$ and to equate $p_{systolic}$ with $V_2 + \Delta_1$ and $p_{diastolic}$ with $V_1$ during the extended period of time.

9. A method as recited in claim 8 further comprising the steps of:
monitoring blood pressure pulses in the detecting step during the extended period of time; and
presenting a visual display of variations in the systolic pressures during the extended period of time.

10. A method as recited in claim 8 wherein the extended period of time immediately follows the measurement cycle.

11. A method as recited in claim 8 wherein the extended period of time is greater than fifteen minutes.

12. A method as recited in claim 8 wherein pulse amplitudes are continuously detected in the detecting step during the extended period of time.

13. A method as recited in claim 8 wherein the detecting step is accomplished using an oximeter, and the measuring step is accomplished using a sphygmomanometer.

14. A tangible computer program product for continuously monitoring the blood pressure of a patient for an extended period of time, wherein the computer program product comprises program sections that, when executed, cause a computer to perform the following method steps: measuring a systolic pressure ($p_{systolic}$) at a time "$t_0$" at the beginning of a measurement cycle; detecting a pulse amplitude value "$V_1$" and a pressure "$p_1$" at a determined time "$t_1$"; establishing an initial pressure drop "$\Delta_1$", from $p_{systolic}$ to $p_1$, at the determined time "$t_1$"; detecting a pulse amplitude value "$V_2$" at a time "$t_2$" at the end of the measurement cycle; comparing a pulse differential "$\Delta_v$" ($\Delta_v = V_1 - V_2$) directly with a pressure differential "$\Delta_p$" ($\Delta_p = p_{diastolic}$) to correlate pulse metrics of $\Delta_v$ with pressure metrics of $\Delta_p$; and equating $p_{systolic}$ with $V_2 + \Delta_1$ and $p_{diastolic}$ with $V_1$ during an extended period of time.

15. A computer program product as recited in claim 14 wherein the extended period of time immediately follows the measurement cycle, wherein the extended period of time is greater than fifteen minutes, and wherein pulse amplitudes are continuously detected during the extended period of time.

* * * * *

UNITED STATES PATENT AND TRADEMARK OFFICE
CERTIFICATE OF CORRECTION

PATENT NO. : 8,951,204 B2  
APPLICATION NO. : 13/464732  
DATED : February 10, 2015  
INVENTOR(S) : Guy P. Curtis Page 1 of 1

It is certified that error appears in the above-identified patent and that said Letters Patent is hereby corrected as shown below:

Claims

Column 8, Line 13, claim 14 - DELETE "$(\Delta_p = p_{diastolic})$" and INSERT -- $(\Delta_p = p_1 - p_{diastolic})$ --.

Signed and Sealed this  
Twenty-seventh Day of October, 2015

Michelle K. Lee  
*Director of the United States Patent and Trademark Office*